United States Patent [19]

Szu et al.

[11] Patent Number: 5,204,098

[45] Date of Patent: Apr. 20, 1993

[54] POLYSACCHARIDE-PROTEIN CONJUGATES

[75] Inventors: Shousun C. Szu; Rachel Schneerson, both of Bethesda; John B. Robbins, Chevy Chase, all of Md.

[73] Assignee: The United States of America as represented by the Department of Health and Human Services, Washington, D.C.

[21] Appl. No.: 155,799

[22] Filed: Feb. 16, 1988

[51] Int. Cl.$^5$ .................. A61K 39/112; A61K 39/385; C07K 17/10
[52] U.S. Cl. ..................... 424/92; 424/85.91; 424/88; 435/961; 530/391.1; 530/395; 530/404; 530/408; 530/807
[58] Field of Search .............. 424/88, 92, 85.91; 530/404, 408, 807, 395, 391.1; 435/961

[56] References Cited

U.S. PATENT DOCUMENTS 4,459,286  7/1984  Hilleman et al. ............... 424/92
4,493,795  1/1985  Nestor, Jr. et al. ............ 530/326
4,695,624  9/1987  Marburg et al. ............... 530/395

OTHER PUBLICATIONS

Szu et al (1987, Nov.) J. Exp. Med. 166:1510–1524.
J. Infect. Dis. 154 (2): 342–345 (1986), Tacket et al.
J. Infect. Dis. 150(3): 436–449 (1984), Robbins et al.
Biochem. Pharmacol. 28: (15) 2297–2302 (1970), Merryman et al.
J. Clin. Microbiol. 12: 22–26 (1980), Nolan et al.
Gann 71 (6): 766–774 (1980), Miyazaki et al.
Donnelly et al (1990) J. Immunol. 145:3071–3079.
Erlanger et al (1980) Methods Enzymol 70:85–104.
Marburg et al (1986) J. Am. Chem. Soc. 108:5282–5287.
McKenzie et al (1984) J. Immunol. 133:1818–1824.
Szu et al (1987) CA 108(24):210120p.

Primary Examiner—Christine M. Nucker
Assistant Examiner—Kay K. Kim
Attorney, Agent, or Firm—Morgan & Finnegan

[57] ABSTRACT

Vi capsular polysaccharides conjugated to toxin-dependent proteins can be used to enhance antibody response and to convert T-dependent properties to the Vi capsular polysaccharide. A heterobifunctional cross-linking agent can be used to bind thiol derivatives of the Vi capsular polysaccharides to the proteins, such as diphtheria, tetanus toxoids, cholera toxin and *Haemophilus influenzae*.

18 Claims, 5 Drawing Sheets

→4)-α-*D*-gal NAc A-(1→
↑3
OAc

HS – (CH₂)₂ – NH₂
cysteamine

₂HN – (CH₂)₂ – S – S – (CH₂)₂ – NH₂
cystamine 1   2   3   4   5   6   7   8

POLYSACCHARIDE-PROTEIN CONJUGATES

FIELD OF THE INVENTION

The present invention relates to immunoprophylaxis and vaccines; more particularly it relates to Vi capsular polysaccharide-protein conjugates which can be used to elicit immune response by producing serum antibodies in a host.

BACKGROUND OF THE INVENTION

Enteric fevers continue to cause considerable morbidity and mortality in countries that have not yet achieved control of sewage disposal and contamination of drinking water. In these countries, the most frequent and serious cause of enteric fevers is *Salmonella typhi* (typhoid fever). Immunoprophylaxis against typhoid fever on a world-wide basis has not been attempted because the two presently available vaccines have limitations. The cellular typhoid vaccines induce only a limited immunity and elicit side reactions that are sufficiently frequent and sever to have discouraged their widespread acceptance. An orally administered attenuated strain of *S. typhi.*, Ty-21a, requires three to four doses to induce about 65% protection. This vaccine is expensive, and its mode of protection has not been identified, which has prevented precise standardization of the vaccine.

Recently, two clinical evaluations, in populations with high rates of typhoid fever (about 1%/annum), have provided evidence that immunization with the capsular polysaccharide of *S. typhi.* (Vi) confers immunity against typhoid fever, cf. Klugman et al., *Abstract 27th ICAAC*, New York, N.Y., 1987; and Acharya et al., Prevention of typhoid fever in Nepal with the Vi capsular polysaccharide of *Salmonella typhi*, in press, 1987. The Vi vaccine, prepared under conditions which did not change its structure, elicited a four-fold or greater rise in serum antibodies in about 75% of children and adults in Nepal and in school children in the Eastern Transvaal, Republic of South Africa. The protective efficacy of the Vi in these two trials was about 70%. In contrast, the same Vi elicited a ≧four-fold antibody rise in 97% of young adults in Q France and the United States. The seroconversion rate and efficacy of other capsular polysaccharides, e.g., meningococcal vaccines, were also lower in Africa than in Finland or the United States. This lesser immunogenicity and efficacy of meningococcal vaccines was attributed to the high burden of infections, including malaria, in the African population. Since the protective response elicited by capsular polysaccharide vaccines is serum antibodies, it could be predicted that a more immunogenic Vi would be more protective against typhoid fever in high-risk populations.

Originally, Avery and Goebel in *J. Exp. Med.* 50:531 (1929) and Goebel in *J. Exp. Med.* 50:469-520 (1929) showed that the immunogenicity of pneumococcus type 3 polysaccharide could be increased by binding it chemically to a carrier protein. This principle has been applied successfully to increase the immunogenicity of capsular polysaccharides of other pathogens.

Robbins et al in *J. Infect. Dis.* 150, 3 436-449 (1984) disclose that a Vi polysaccharide used for immunizing humans against experimental challenge with *S. typhi.* failed to prevent typhoid fever. The conditions used to prepare the vaccine presumably denatured it and reduced its immunogenicity. There is no disclosure that this polysaccharide could be coupled to other proteins.

Tacket et al, in *J. Infect. Dis.* 154 2 342-345 (1986), disclose a vaccine made from the Vi capsular polysaccharide of *Salmonella typhi*, but this vaccine is not conjugated to a protein.

Miuazake et al., in Gann 71 6 766-774 (1980), disclose a method of preparing an antibody-ricin A-chain conjugate by introducing sulfhydryl groups into RAMIgG, and then reacting this modified antibody with ricin A-chain. This conjugate is said to have cytotoxicity.

Merryman et al., in *Biochem. Pharmacol.* 28 15 2297-2302 (1979), disclose that the proliferative response of human lymphocytes can be altered by the sulfhydryl agents D-penicillamine and 5-thiopyridoxine.

Nolan et al., in *J. Clin. Microbiol.* 12 22-26 (1980), disclose an assay for serum antibody to the *Salmonella typhi* capsular polysaccharide. There is no disclosure that this polysaccharide can be conjugated to any proteins.

SUMMARY OF THE INVENTION

It is an object of the present invention to overcome deficiencies in the prior art, such as those noted above.

It is a further object of the present invention to produce Vi capsular polysaccharide protein conjugates which enhance the antibody response of a host.

It is another object of the present invention to provide an improved vaccine for protection against typhoid fever.

It is yet another object of the present invention to increase the immunity of humans to *Salmonella typhi.*

It is yet a further object of the present invention to produce Vi capsular polysaccharide protein conjugates which confer T-dependent properties to Vi capsular polysaccharides.

According to the present invention, methods are provided to synthesize Vi capsular polysaccharide-protein conjugates in order to enhance antibody response and to confer T-dependent properties to the Vi capsular polysaccharide.

According to the present invention, a heterobifunctional crosslinking agent is used to bind thiol derivatives of the Vi capsular polysaccharide to proteins, yielding Vi-protein conjugates. The process can be used for proteins such as diphtheria, cholera, and tetanus toxoids. The process of the invention can also be used to synthesize protein conjugates with other polysaccharides that have carboxyl functions.

According to the present invention, Vi-protein conjugates can be synthesized in order to enhance the antibody response and to confer T-dependent properties to the *Salmonella typhi* Vi, and to increase its protective action in populations at high risk for typhoid fever.

According to the present invention, a heterobifunctional crosslinking reagent can be used to bind thiol derivatives of the Vi to proteins.

DETAILED DESCRIPTION OF THE INVENTION

Figure 1A:
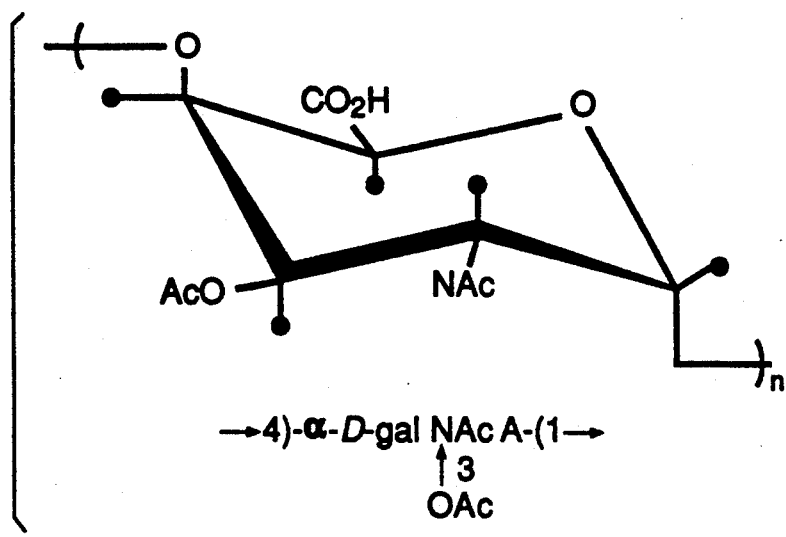
FIG. 1a shows the structure of the repeating unit of the Vi capsular polysaccharide of *Salmonella typhi.*

The present invention provides a method for conjugating capsular polysaccharides having carboxyl groups to a protein. A thiol derivative of the polysaccharide is formed, and the thiol derivative is then bonded to a protein using a hetereobifunctional cross-linking agent, such as N-succinimidyl 3-(-2-pyridyldithio)propionate. The capsular polysaccharide can be Vi capsular polysaccharide. Among the proteins that can be so conjugated are tetanus toxoid, diphtheria toxoid, cholera toxin, Haemophilus influenzae type b protein, and IgG.

Compositions can be produced from the conjugated capsular proteins in a pharmaceutically acceptable carrier which can be used to enhance the antibody response of a host. Preferably, the host is injected with the composition at least two times at two week intervals.

In order to synthesize covalent bonds between the Vi and proteins according to the present invention, Vi, a linear homopolymer of -4-D0a0NacGa1A-1, was O-acetylated up to 90% at C3. The scheme used to prepare these conjugates used the carboxyl function of the NacGalA to form a thiol derivative. This thiol derivative was combined with proteins derivatized by the thiol-active compounds, N-succinimidyl-3-(-2-pyridyldithio)propionate, hereinafter SPDP.

Vi Capsular Polysaccharide

The Vi used for the conjugates was prepared from *Citrobacter freundii,* strain WR 7-11. The *C. Freundii* was cultivated in media containing yeast extract dialysate as described by Hornick et al. in *Trans. Amer. Clin. Climat. Ass.* 78:70 (1966). The Vi was precipitated from the culture supernatant with 1% hexadecyltrimethyl ammonium bromide and sequentially treated with DNase, RNase, and then pronase.

The enzyme-treated product was purified with cold phenol, and the lipopolysaccharide was removed by centrifugation at 35,000, 10° C., for five hours. The Vi was dialyzed exhaustively against pyrogen-free water and freeze-dried.

Vi from *S. typhi* was prepared by a modification of this method. The final products contained less than 1% protein or nucleic acid, and less than 0.01% lipopolysaccharide as measured by SDS-PAGE. The molecular size of the Vi preparations was heterogeneous. The main peak had a molecular size greater than $5 \times 10^3$ Kd as estimated by gel filtration through Sephacryl S-1000 equilibrated in 0.2M NaCl. A lower molecular size Vi, about 65,000, was prepared by ultrasonic irradiation.

Proteins

Bovine serum albumin (BSA) and cholera toxin were used without further purification. Tetanus toxoid and diphtheria toxoid were further purified by gel filtration through Sephacryl S-300. The fractions, corresponding to the molecular weight of the two toxoids, were concentrated by ultrafiltration and passed through 0.45 micron filters. Cholera toxin was additionally characterized for toxicity by the CHO cell assay and by the intradermal rabbit skin test.

Direct binding of Vi to proteins

Vi was bound to diphtheria toxoid by the method of Beuvery et al., as reported in *Infect. Immun.* 37:15 (1982). Equal volumes of Vi and diphtheria toxoid, containing 10 mg/ml each, were mixed, the pH was adjusted to 5.0 with 0.1N HCl, and 1-ethyl-3-(3-dimethylaminopropyl)carbodiimide, also referred to as EDAC, was added to a final concentration of 0.1M.

The pH was maintained at 5.0 by addition of 0.1N HCl for three hours at room temperature. The reaction mixture was stirred at 3°-8° C. for an additional 24 hours, was dialyzed against 0.2M NaCl for 48 hours, and was then centrifuged at 10,000 g for two hours at 3°-8° C.

The supernatant fluid was subjected to gel filtration through 4B-Sepharose equilibrated in 0.2M NaCl. The fractions were monitored by refractometry and by absorption at 2800 A. The void-volume fraction, which contained the Vi-DTI conjugate, were polled, made up to 0.01% in thimerosal, and stored at 3°-8° C.

Synthesis of Vi-Protein Conjugates

The Vi was allowed to dissolved overnight at 3°-8° C. at a concentration of 10 mg/ml in 0.2M NaCl. Cystamine or cysteamine at twice the weight of the Vi was then added as a powder to the Vi solution, The pH of the reaction mixture was adjusted to 4.9 by the addition of 0.1N HCl until the pH was stabilized. The reaction mixture was then dialyzed exhaustively against distilled water at 3°-8° C. and freeze-dried. The extent of thiolation was estimated by the iodoplatinate assay using cystamine as the reference. The thiol ester content was quantitated after reduction of the Vi derivative with DTT and passage of the reaction mixture through Bio-Gel to remove the low molecular weight materials. The material eluted in the void volume was then assayed for its SH content using cysteamine as a standard.

The proteins were next derivatized with SPDP, N-succinimidyl 3-(2-pyridyldithio)propionate. Protein solutions were made within a range of from 5 to 20 mg/ml. Free SH groups were blocked by treatment with 0.01M iodoacetic acid. The reaction mixture, containing the iodoacetic acid and the protein, was incubated at room temperature for one hour, and then equilibrated against 0.15 M HEPES, 5 mM EDTA, pH 7.55 (HE buffer) by dialysis overnight at 3°-8° C. SPDP in an amount of 20 mM in 99.5% ethanol, was added to the protein solution with stirring. The final molar ratio of SPDP to protein ranged form 5 to 24, depending upon the extent of derivatization desired. The reaction was allowed to proceed for one hour at room temperature.

The excess reagent was removed by dialysis against HE buffer overnight at 3°–8° C., followed by gel filtration through Bio-Gel P10 in HE buffer. The void volume was pooled, concentrated to 5–10 mg/ml and stored at 3°–8° C. The molar ratios of 2-pyridyl disulfide in the derivatized protein were determined by reducing the disulfide bond in 50 mM dithiothreitol and calculating the amount of pyridine-2-thione released by using the extinction coefficient for pyridine of $9.08 \times 10^3$/mol/cm at 3430 A.

Synthesis of Vi-Protein Conjugates

To synthesize the Vi-protein conjugates, the cystamine derivative of Vi was dissolved in HE buffer at 5 to 10 mg/ml. Dithiothreitol was added to a final concentration of 100 mM and stirred for one hour at room temperature. After dialysis against HE buffer for two hours, the reaction mixture was then passed through a BioGel P10 column, equilibrated with HE buffer, and the void volume peak was concentrated by ultrafiltration under $N_2$ pressure. SPDP-derivatized protein was added to the reduced Vi derivative to achieve an equimolar ratio of N-pyridyl disulfide groups and SH groups. The reaction mixture was flushed with nitrogen and allowed to incubate at room temperature for one hour, and then at 3°–8° C. for 24 hours. The release of pyridine during the reaction was measured by the change in optical density at 3430 A.

The reaction mixture was concentrated by ultrafiltration as described above and subjected to gel filtration through Sephacryl S-1000 in 0.2M NaCl at room temperature. The void volume fractions were pooled, concentrated by ultrafiltration, dialyzed against 0.15M NaCl, 0.01% thimerosal, 1 mM EDTA, pH 7.0, and stored at 3°–8° C. The protein concentration of the conjugate was determined by the Bio-Rad Coomassie Blue assay using the SPDP-derivatized protein as the standard. The concentration of protein and Vi in the conjugates were also determined by Fourier transformed infrared spectroscopy (FTIR) and by spectrophotometric titration by acridine orange.

Pneumococcus type 6B-tetanus toxoid conjugate (Pn6B-TT)

Pneumococcus type 6B capsular polysaccharide was derivatized with adipid acid dihydrazide and bound to tetanus toxoid as described by Chu et al., *Infect. Immun.* 40:245 (1983); Schneersonn et al., *op. cit.* 45:582 (1984); and Schneerson et al., *op.cit.* 52:501 (1986). The protein/polysaccharide ratio of this preparation was 2.8.

Immunization of Mice

Female, weanling, BALB/c mice, weighing 16–20 grams, were injected subcutaneously with 0.1 ml of either Vi, Vi conjugates, or saline 1, 2, or 3 times at two week intervals. Mice from each experimental groups were exsanguinated ten days after each injection. Alum-adsorbed Vi-$CT_{XII}$ was prepared with Alhydrogel. The Alhydrogel was centrifuged and Vi-$CT_{XII}$ was added to the pellet to achieve a final concentration of 0.5 mg aluminum/ml and 5.0 micrograms of Vi as a suspension. This mixture was tumbled overnight at room temperature and then stored at 3°–8° C.

Immunization of Primates

Juvenile Rhesus monkeys were injected subcutaneously twice one month apart with 0.5 ml of Vi or Vi-CTXII containing 25 micrograms of Vi. Controls were injected with Pn6B-TT containing 15 micrograms of capsular polysaccharide. The monkeys were bled before and three weeks after each injection.

Immunological Methods

Serum Vi antibodies were measured by radioimmunoassay and expressed as micrograms Ab/ml. The differences between the levels of antibodies in experimental groups were calculated by Fisher's exact T-test. The results were tabulated as the geometric means and 80% confidence limits. Antibodies to cholera toxin were measured by ELISA. Rabbit anti-BSA serum was obtained from Cappel Laboratories, Cochranville, Pa. Hyperimmune burro antiserum (B-260) containing 660 micrograms /vi Ab/ml, was prepared by multiple intravenous injections of formalin-fixed *S. typhi* Ty2 as described by Nolan et al. in *J. Clin, Microbiol.* 12:22 (1980). The preparation and characterization of burro 241, hyperimmune cholera toxin antiserum, containing 16.5 mg Ab/ml. was reported by Dafni et al., *J. Infect. Dis.* 133:S138 (1976). Rocket immunoelectrophoresis and immunodiffusion were performed as described by Szu et al., supra.

FTIR Spectroscopy

The composition of the conjugates was determined using the Vi and proteins as references. One mg of Vi, carrier protein, or Vi conjugate was added to 100 mg of KBr and dissolved in 2.0 ml distilled water. The sample was freeze-dried and pressed into a pellet. FTIR spectra were recorded on a Nicolet 7199 spectrometer and analyzed as described by Tackett et al., *J. Infect. Dis.* 154:342 (1986).

$^{13}C$ Nuclear Magnetic Resonance

The $^{13}C$ NMR spectra of the Vi (20 mg/ml D2) were recorded at 60° C. in a Nicolet spectrometer. A 5.0 mm sample cell was used and the spectrometer operated at 67.9 MHz in the pulse Fourier transformed mode with complete proton decoupling and quadrature phase detection. A 4-Hz line broadening was applied to the signal prior to Fourier transformation to enhance the signal-to-noise ratio.

SDS-PAGE

The molecular weights of the proteins and their Vi conjugates were assayed in 7.5% polyacrylamide gels. Samples containing 5 to 10 micrograms of protein with or without 2-ME were electrophoresed concurrently with protein standards. The gels were stained with Coomassie Blue.

Results

Figure 2:
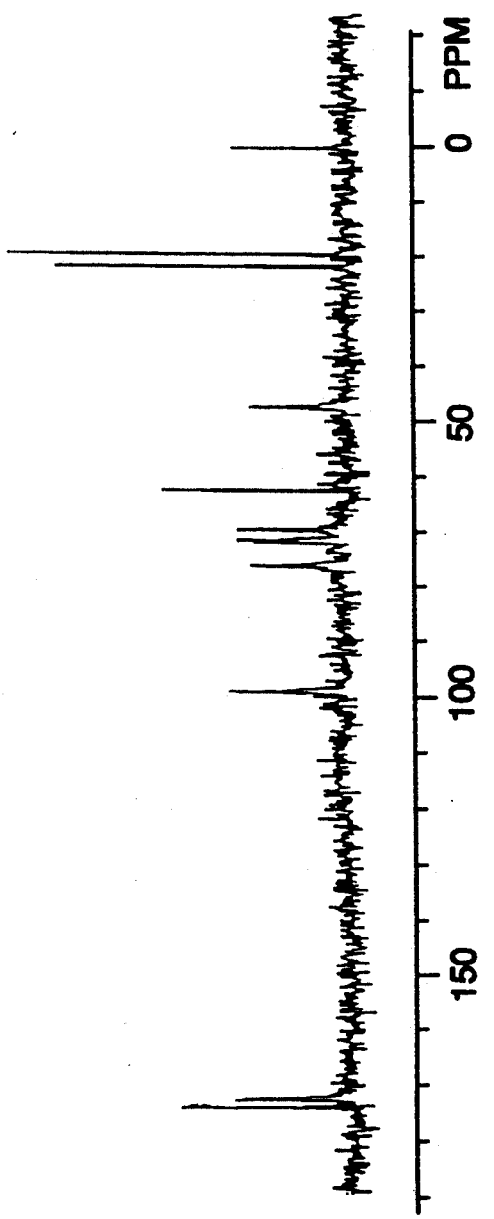
FIG. 2 shows the $^{13}C$ NMR chemical shift of Vi depolymerized by ultrasonic irradiation (molecular weight 65,000, conc. 20 mg/ml), downfield from $^{13}C$-enriched acetonitrile used as an internal standard. The spectra were recorded for a D$_2$O solution in a 5-mm tube with a Nicolet 270 spectrometer operating at 67.89 MHz in pulse Fourier transformed mode.

The Vi from *S. typhi* and some strains of *C. freundii* is a linear homopolymer of NacGalA acid, variably O-acetylated at the C3 position. FTIR and $^{13}C$ NMR spectroscopy showed that the structures of the Vi from the strain of *C. freundii* and the Ty2 strain of S. typhi used were indistinguishable. Immunodiffusion analyses showed a reaction of identity between Vi polysaccharides from *C. freundii* and *S. typhi* when reacted with B-260 anti Vi antiserum. The Vi used for immunization and for synthesis of the conjugates in the examples described herein contained about 80% O-acetyl/mole repeating unit as determined by $^{13}C$ NMR, as shown in FIG. 2. Since the Vi has no vicinal hydroxyl groups, the carboxyl served as an activation site in the strategy for the conjugation reaction.

The first Vi conjugates were prepared with EDAC, which catalyzed the direct conjugation between the carboxyl groups of Vi and the amino groups of diphtheria toxoid. The yield from this reaction, illustrated by a representative product Vi-DT$_I$, was about 3% of the starting materials. Vi antibody levels elicited in mice by this conjugate and by the two controls, Vi and saline, are given in Table 1.

There were no Vi antibodies in pre-immune sera or from mice injected with saline (controls) in this and subsequent experiments. Dosages of 0.5, 5.0, or 50.0 micrograms of Vi elicited similar levels of antibodies after the first, second, and third injections (the slightly higher levels of antibodies in the group injected with 5.0 micrograms of Vi after the third injection were not statistically different). The levels of antibodies after the second and third injections of 5.0 or 50.0 micrograms of Vi-DT$_I$ were about seven-fold higher than those elicited by the Vi alone (p=0.001). Each of the three dosages of Vi-DTI elicited a booster response after the second injection. No differences in the levels of antibodies elicited by the 5.0 and 50.0 micrograms doses of Vi-DT$_I$ were observed; both of these doses were more immunogenic than 0.5 micrograms of this conjugate after the first injection only (p=0.001).

Vi protein conjugates with SPDP

An alternate conjugation procedure, that of covalently bound thiolated derivatives of the Vi and the SPDP-derivatized proteins, was studied in order to increase the yield and immunogenicity of the Vi conjugates.

Figure 1B:
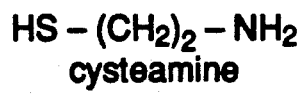
FIG. 1b shows the structure of cysteamine.
Figure 1C:
FIG. 1c shows the structure of cystamine.

Introduction of thiol groups onto the Vi was attempted by forming amide bonds between the amino groups of cysteamine (FIG. 1b) and the carboxyl groups of the Vi in the presence of EDAC. The yield of thiol added to the Vi by this scheme was less than 1% w/w, probably because the SH groups of cysteamine were oxidized. To avoid this possibility, cystamine was used. The thiols of cystamine are linked by disulfide bonds and are thus protected from oxidation, cf. FIG. 1 C. Using EDAC to catalyze amide bond formation, about 6% w/w of cystamine was bound to the Vi. After reduction of the disulfide bonds by dithiothreitol, the yield of thiol esters was 0.5-2% of the repeating monosaccharide. The freeze-dried cystamine derivative of the Vi was stable at −20° C.

Figure 3A:
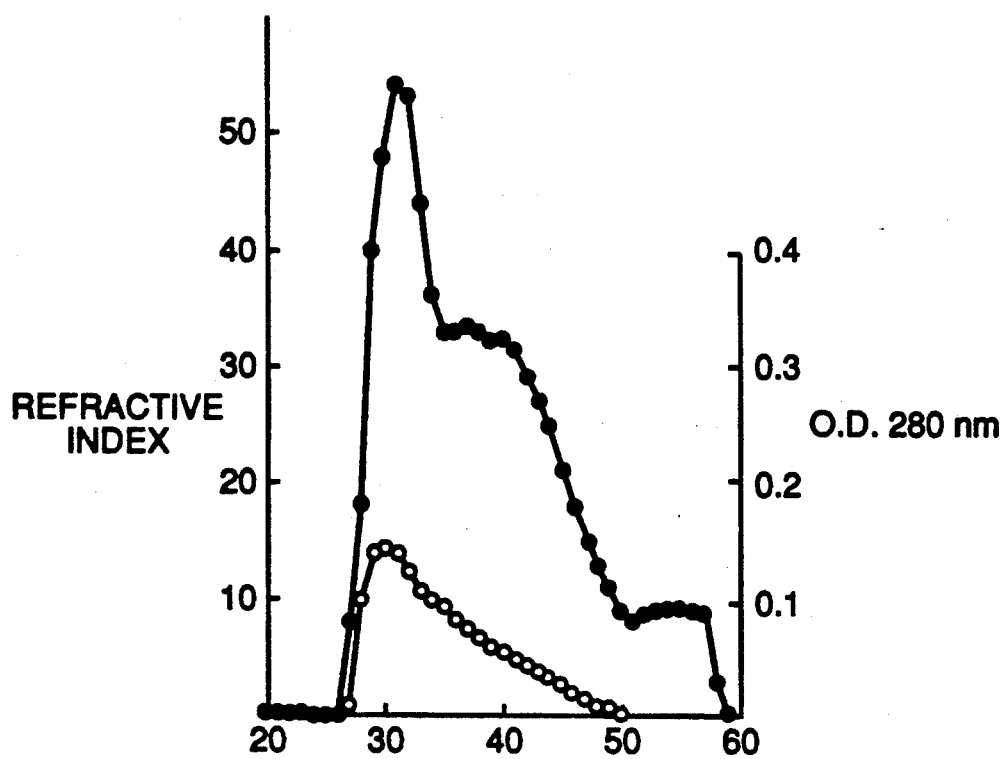
FIG. 3 shows the gel filtration profile of Vi-CT$_{XII}$ and its components, Vi and CT, through s1000 Sephacryl equilibrated in 0.2M NaCl. In chart A, the conjugate—, refractive index—, O.D. 2800 A. In chart B, Vi-cystamine∆—∆, refractive index, and CT∆—∆, O.D. 2800 A.
Figure 3B:
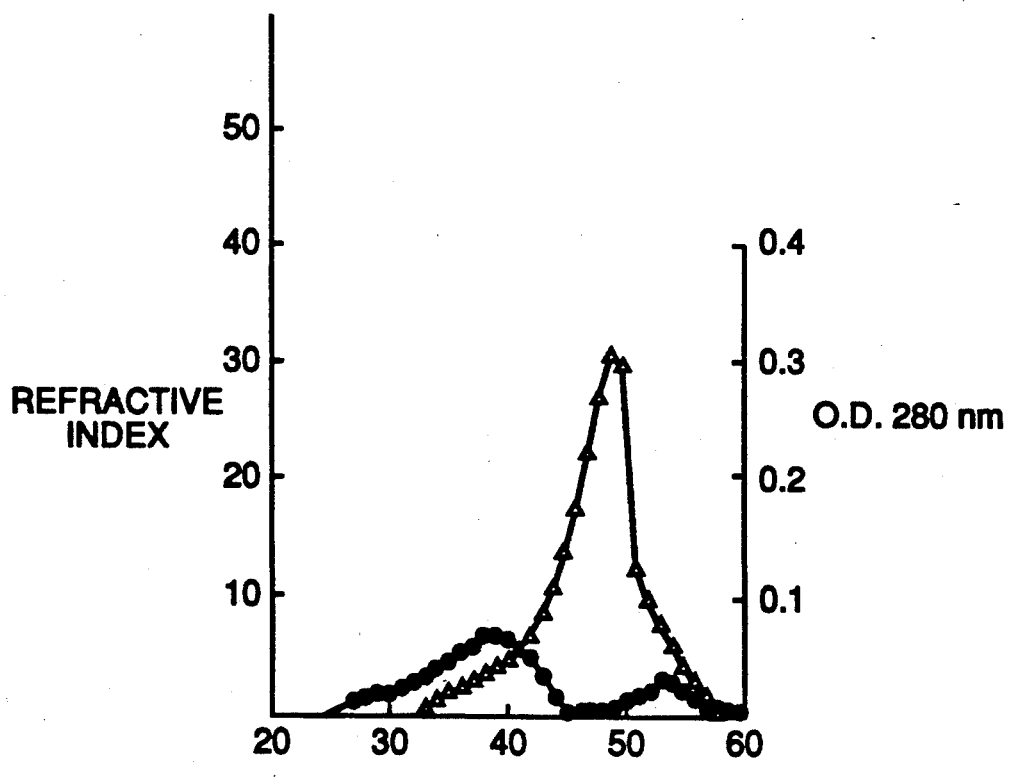

Physico-chemical characterization of the Vi capsular polysaccharide conjugates The disulfide bonds of the Vi capsular polysaccharide-cystamine derivative were reduced with dithiothreitol prior to the conjugation reaction. The molecular size of a representative conjugate, Vi-CTV$_{III}$, (Kd<0.1) was larger than that of the proteins (Kd=0.64) or the Vi capsular polysaccharide (Kd=0.36) as illustrated by the gel filtration profile in FIG. 3. The composition of the thiolated Vi capsular polysaccharide, the SPDP-protein derivatives, and the conjugates used in these studies are listed in Table 2.

TABLE 2

Characterization of Vi-protein conjugates prepared with N-succinimidyl 3-(2-pyridylthio) propionate (SPDP).

| Conjugate | Yield* | SH/Vi (% w/w) | SPDP/protein (mol/mol) | SPDP/protein (wt/wt) | Protein/Vi (wt/wt) |
|---|---|---|---|---|---|
| Vi-BSA$_{IV}$ | 63.0 | 1.2 | 17.0 | 0.078 | 0.7 |
| Vi-CT$_{VIII}$ | 5.4 | 1.0 | 5.4 | 0.019 | 0.4 |
| Vi-CT$_{XII}$ | 18.0 | 0.5 | 4.5 | 0.016 | 1.5 |
| Vi-CT$_{XV}$ | 14.9 | 0.5 | 5.0 | 0.024 | 1.6 |
| Vi-CT$_{XX}$ | 16.8 | 0.4 | 3.8 | 0.018 | 1.5 |
| Vi-TT$_{XXV}$ | 6.2 | 0.7 | 12.0 | 0.025 | 1.4 |

*Percent of Vi recovered in conjugate

Figure 4:
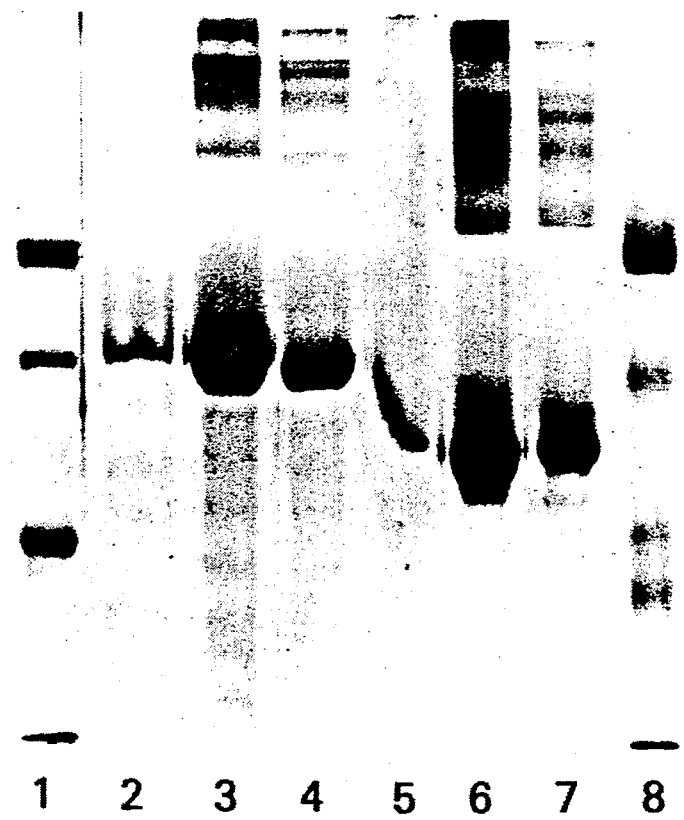
FIG. 4 shows polyacrylamide gel (7.5%) electrophoresis pattern of bovine serum albumin and its conjugate with Vi. Lanes 1 to 4 show the migration pattern of samples reduced by 2-ME, lanes 5 to 8 represent samples not treated by 2-ME. Lanes 2 and 5 show Vi-BSA$_{IV}$, lanes 3 and 6 show BSA-SPDP, lanes 4 and 7 show BSA, and 1 and 8 show protein standards.
Figure 5:
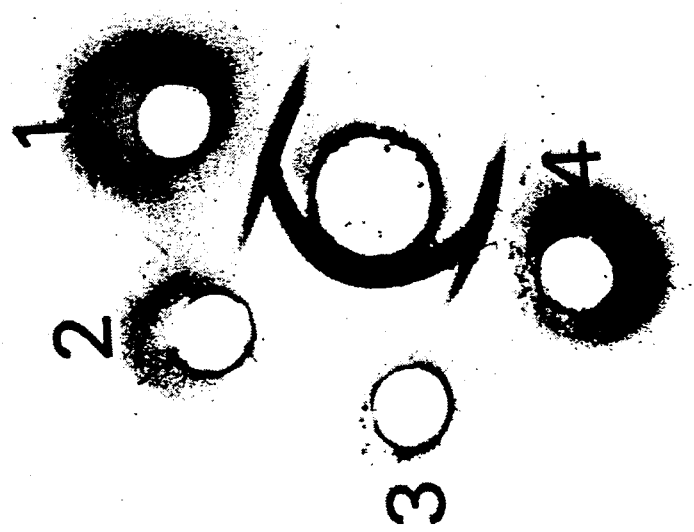
FIG. 5 shows the immunodiffusion pattern of Vi-BSA$_{IV}$ conjugate reacting with various antisera in 1% agarose gel. The center well contained 15 microliters of Vi-BSA$_{IV}$ (0.5 mg/ml). Wells 1 and 4 Burro 260 anti-S.typhi Ty2 antiserum, wells 2 and 3, rabbit anti-BSA antiserum.

The change in the molecular size of the intermediate and final products of the conjugation reaction was further analyzed by SDS-PAGE, as shown in FIG. 4. The BSA-SPDP derivative exhibited a pattern similar to that of native BSA, demonstrating that aggregation did not occur during the reaction with SPDP. The Vi-BSA$_{IV}$, as did all of the Vi capsular polysaccharide conjugates, failed to enter the gel, probably due to its large size. Vi-BSA$_{IV}$, reduced with 2-ME, exhibited a band similar to the native BSA, indicating that the Vi capsular polysaccharide was bound to this protein by a disulfide bond.

Antigenic Analysis

The Vi capsular polysaccharide conjugates were analyzed by immunodiffusion with antisera to each of its components. The anti-Vi and anti-BSA sera formed a partial identity reaction with the conjugate, indicating that the Vi capsular polysaccharide and BSA were covalently bound. The Vi capsular polysaccharide antiserum reacted with the Vi capsular polysaccharide and Vi-BSAIV with a partial identity reaction. A spur of precipitation overrode the Vi capsular polysaccharide line onto the reaction of the antiserum with the Vi-BSA (not shown). Conjugates prepared with diphtheria toxoid, tetanus toxoid, and cholera toxin failed to react with their homologous anti-protein antisera by immunodiffusion but did precipitate with these antisera by rocket immunoelectrophoresis (not shown).

TABLE 1

Serum antibody responses of female BALB/c mice injected with Vi or with Vi-diptheria toxoid conjugate (Vi-DT$_I$) prepared with using EDAC as the coupling reagent.

| Vaccine | Dose (ug) | ug Vi Ab/ml (geometric mean, 80% confidence limits) 1st | | 2nd | | 3rd | |
|---|---|---|---|---|---|---|---|
| Vi | 0.5 | 0.19$^a$ | (0.05–0.72) | 0.61 | (0.30–1.23) | 0.47 | (0.19–1.15) |
| Vi | 5.0 | 0.56 | (0.28–1.11) | 0.43$^e$ | (0.13–2.33) | 1.11 | (0.29–4.26) |
| Vi | 50.0 | 0.31$^c$ | (0.13–0.75) | 0.24$^g$ | (0.04–1.47) | 0.20$^i$ | (0.04–0.97) |
| Vi-DT$_I$ | 0.5 | 0.07$^b$ | (0.04–1.12) | 0.31 | (0.06–1.52) | 0.79 | (0.28–2.24) |
| Vi-DT$_I$ | 5.0 | 0.63$^k$ | (0.30–1.30) | 2.79$^f$ | (0.65–12.0) | 2.85$^f$ | (1.09–7.46) |
| Vi-DT$_I$ | 50.0 | 1.40$^d$ | (0.80–2.45) | 2.65$^h$ | (0.69–10.1) | 3.00$^j$ | (1.39–6.46) | a vs b: p = 0.0014, b vs k,d: p = 0.001, c vs d, e vs f: p = 0.001, g vs h, i vs j: p = 0.0001, k vs f: p = 0.003

Mice were injected s.c. 2 wks. apart with 0.1 ml of each vaccine or saline. 8 mice were for each experimental group, 10 days after each injection mice were exsanguinated and their sera assayed for Vi antibodies by RIA [9]. Results are expressed as the geometric mean and 80% confidence limits.

Residual Toxicity of Vi-CTX$_{III}$ Conjugate

The toxicity of cholera toxin was reduced by its conjugation to Vi capsular polysaccharide. A $10^4$-fold reduction was observed in the CHO cell assay. The skin test in rabbits, however, showed only a $10^3$-fold reduction in toxicity. Although injection with 0.5 ml of Vi-CT$_{XII}$ (1 human dose) had no effect on mice, injection of 5.0 ml of Vi-CT$_{XII}$ intraperitoneally resulted in the death of two of three guinea pigs. This conjugate, therefore, did not pass the safety requirements of CFR 600:16.

antibodies after the first injection, and there were no booster responses after the second or third injections.

There were differences in the immunogenicity of conjugates prepared with the same components. The first injection of Vi-CT$_{VIII}$ and Vi-CT$_{XII}$ induced about a thirty-fold increase in cholrea toxin antibodies, which also rose four-fold after the second and third injections. Vi-CT$_{XII}$ elicited higher levels of cholera toxin antibodies, as well as Vi capsular polysaccharide antibodies, than Vi-CTV$_{III}$.

Table 4 shows the immunogenicity in juvenile Rhesus monkeys.

TABLE 4

Serum antibody responses of juvenile Rhesus monkeys immunized with Vi, Vi conjugated to cholera toxin (Vi-CTXII), or pneumococcus polysaccharide type 6B conjugated to tetanus toxoid (Pn6B-TT).

| Vaccine | n = | ug Ab/ml Geometric mean (80% confidence limits) | | |
|---|---|---|---|---|
| | | Pre-immune | 1st injection | 2nd injection |
| Vi | 6 | 0.07 (0.05–0.10) | 0.23$^d$ (0.06–0.82) | 0.07$^e$ (0.05–0.09) |
| Vi-CT$_{XII}$ | 8 | 0.07$^a$ (0.03–0.19) | 0.93$^b$ (0.24–3.55) | 3.65$^c$ (0.72–18.5) |
| Pn6B-TT | 8 | 0.08 (0.06–0.11) | 0.10 (0.05–0.21) | 0.10 (0.04–0.23) | a vs b: p = 0.004, b vs c: p = 0.02, a vs c: p = 0.0003, b vs d: p = 0.009, c vs e: p = 0.001.
Monkeys were immunized s.c. with 0.5 ml containing either 25 ug of Vi or 15 ug of Pn6B-TT at 3 wks intervals. The monkeys were bled before each injection and 3 wks. after the last injection. Vi antibodies, measures by RIA [9], are expressed as geometric means and 80% confidence limits.

Immunogenicity in Laboratory Animals

Table 3 shows the immunogenicity of mice.

TABLE 3

Serum antibody responses of mice injected with the Vi or Vi conjugates with bovine serum albumin (BSA), cholers toxin (CT), or diptheria toxoid (DT) or tetanus toxoid (TT) cross-linked with SPDP.

| Immunogen | n = | ug Ab/ml Geometric mean (80% confidence limits) | | |
|---|---|---|---|---|
| | | 1st injection | nd injection | 3rd injection |
| Vi | 7 | 0.56$^d$ (0.22–1.43) | N.D.$^a$ | N.D. |
| Vi-BSA$_{IV}$ | 7 | 2.86$^e$ (1.24–6.53) | N.D. | N.D. |
| Vi-CT$_{VIII}$ | 4 | 1.35$^f$ (0.27–6.71) | 4.53 (2.74–7.46) | N.D. |
| Vi-CT$_{XII}$ | 10 | 2.12$^g$ (1.29–3.47) | 9.04$^m$ (4.84–16.9) | 6.28$^n$ (1.98–19.9) |
| Vi-CT$_{ads}^b$ | 10 | 1.01$^h$ (0.57–1.79) | 1.16 (0.54–2.53) | 0.87 (0.37–2.07) |
| Vi-CT UD$^c$ | 10 | 2.94$^i$ (1.55–5.55) | 4.23 (1.75–10.2) | N.D. |
| Vi-DT$_{XV}$ | 10 | 2.57$^j$ (1.27–5.17) | 4.61 (2.49–8.52) | N.D. |
| Vi-DT$_{XX}$ | 10 | 1.76$^k$ (0.93–3.38) | 1.26 (0.63–2.52) | N.D. |
| Vi-TT$_{XXV}$ | 9 | 2.56$^l$ (1.40–4.69) | 3.15 (1.71–5.80) | 4.18 (2.74–6.36) |

Female, 16–20 g, BALB/c mice were injected s.c. with 0.2 ml containing 2.5 ug Vi alone or Vi conjugate 2 wks aparts. Mice of each group were exsanguinated 10 days after their last injection and Vi antibodies measured by RIA [59].
$^a$N.D.—Not done.
$^b$Adsorbed onto aluminum hydroxide, 0.5 mg Al+++/ml.)
$^c$Molecular size of Vi reduced to 65,000 by ultrasonic irradiation [57].
d vs e,g,i,j,k,l: p = 0.001, d vs f: p = 0.002, d vs h: p = 0.04, m vs g: p = 0.0003, n vs g: p = 0.003

None of the pre-immunization sera or sera from mice injected with saline had detectable levels of Vi capsular polysaccharide antibodies. All of the conjugates elicited higher levels of antibodies than the Vi capsular polysaccharide alone (p=0.001). The highest level of antibodies after the first injection were elicited by the Vi-CT prepared from the Vi capsular polysaccharide depolymerized by ultrasonic irradiation, but these differences were not statistically significant. Booster responses after the second injection, as defined by a four-fold or greater increase in the geometric mean antibody levels, were observed in the animals injected with all of the conjugates except the Vi-CT adsorbed. Vi-TT$_{XXV}$ also elicited an increase in antibodies after the third injections. The levels in this group, however, were similar to those observed with the other conjugates after two injections. The poorest response was elicited by Vi-CT$_{XII}$ adsorbed; this preparation elicited the lowest levels of A single injection of Vi capsular polysaccharide elicited Vi capsular polysaccharide antibodies in five of the six monkeys tested (p=0.004). The levels of Vi capsular polysaccharide antibodies declined in all six monkeys following the second injection of the Vi capsular polysaccharide. Seven of the eight monkeys injected with Vi-CT$_{XII}$ responded with about a twenty-fold increase in antibodies after the first injection. The one non-responding monkey had a pre-immune level of 0,35 micrograms antibody/ml. The second injection of the conjugate in this group elicited about a three-fold increase over that induced by the first injection of Vi-CT$_{XII}$ (p=0.002) and about 60 times the pre-immunization level (p=0.003). The monkey that did not respond to the first injection of Vi-CT$_{XII}$ had a two-fold increase in antibodies after the second injection. No change in Vi capsular polysaccharide antibodies was observed after injection of the Pn6B-TT (control).

The above evidence demonstrates that antibodies elicited by Vi capsular polysaccharide confer immunity against typhoid fever. The pathogenic and protective roles of the Vi are, therefore, similar to the capsular polysaccharide of other encapsulated bacterial pathogens, despite the controversy over the pathogenic and protective roles of the Vi capsular polysaccharide in typhoid fever.

The main protective immune response elicited by capsular polysaccharides according to the present invention is serum antibodies. Both the seroconversion rates and post-immunization levels of antibodies induced by capsular polysaccharides have been correlated with their protective actions.

Serum antibody responses induced by Vi capsular polysaccharide in inhabitants of areas where typhoid fever is endemic, where there is also a high rate of malnutrition and other acute and chronic infectious diseases, are less than optimal. Accordingly, the Vi capsular polysaccharide was covalently bound to toxin-dependent proteins both to increase its immunogenicity and to confer upon it the properties of T-dependency. This synthesis offers several advantages:

1. There is no cross-linking of either component;
2. the reactions are conducted in aqueous solutions at neutral pH;
3. the synthesis is applicable to other polysaccharides with carboxyl functions;
4. the carrier protein is only slightly modified and can elicit antibodies to the native protein.

The resultant conjugates elicited higher levels of antibodies than the Vi capsular polysaccharide alone, and induced a booster response in weanling mice and juvenile primates. Similar studies of *Haemophilus influenzae* type b-protein conjugates were predictive of their enhanced antibody responses in humans.

IgG Vi capsular polysaccharide antibodies protected mice challenged with *S. Typhi*. Indirect evidence has been provided that the Vi capsular polysaccharide elicited IgG antibodies in humans. Because *H. influenzae* type b-protein conjugates elicit IgG CPS antibodies, it is likely that Vi conjugates will also elicit IgG antibodies.

Convalescence from typhoid fever does not always confer immunity to *S. typhi*. Tsang et al. in *J. Clin. Microbiol.* 25: 531 (1987), reported that the Vi capsular polysaccharide alone was a better immunogen in mice than *S. typhi* strain 560Ty. Increasing evidence points to superior immunogenicity of capsular polysaccharide-protein conjugates compared to that of the homologous bacteria in certain circumstances, viz:

1. Conjugates of *H. influenzae* type b elicit higher levels of capsular polysacchaide antibodies in infants and young children than do systemic infections;
2. one to three injections of these conjugates elicited higher levels of antibodies in mice than that elicited by the homologous bacteria.

Unlike the capsular polysaccharide of many encapsulated bacterial pathogens, Vi capsular polysaccharide induced serum antibodies and conferred protection against lethal challenge with *S. typhi* in mice. Reinjection of Vi capsular polysaccharide did not induce a booster effect in mice. In Rhesus monkeys, reinjection reduced the levels of Vi capsular polysaccharide antibodies. Immunized chimpanzees had no detectable Vi capsular polysaccharide antibodies, and were not protected against challenge with *S. typhi*.

The serum antibody responses elicited by conjugates prepared with SPDP were higher than those prepared by direct binding with EDAC. An explanation for this finding is that cross-linking reagents, such as SPDP, form conjugates with a "spacer" between the two macromolecules. This property may enable a more effective interaction between the carrier protein and helper T-lymphocytes.

The higher levels of Vi capsular polysaccharide antibodies elicited by the Vi-CT conjugates could be explained by the adjuvant effect exerted by the residual activity (toxicity) of the cholera toxin. The formation of a conjugate with the Vi capsular polysaccharide reduced the toxicity of the cholera toxin about $1.0 \times 10^3$ to $1.0 \times 10^4$-fold. The resultant toxicity was lethal for the guinea pig but not for the mice and monkey. The residual toxicity did not pass the general safety test for bacterial vaccines described in the Code of Federal Regulations. This was probably due to the greater sensitivity of guinea pigs to the lethal effects of cholera toxin.

*S. typhi* is an inhabitant of and a pathogen for humans only; there are yet no animal models or in vitro correlates of immunity that could be used to predict the protective activities of Vi capsular polysaccharide-conjugates. Only the mucin-enhanced lethal infection of mice has been shown to correlate with the clinical effectiveness of cellular typhoid vaccines. The mouse protection model has been shown to be a measure of Vi capsular polysaccharide antibodies, whether actively induced or passively administered. The Vi capsular polysaccharide antibody response has been measured herein by the response induced by the conjugates in laboratory animals by radioimmunoassay rather than by this bioassay.

The Vi capsular polysaccharide has proven to be a protective antigen in two double based, controlled clinical trials in areas with high rates of typhoid fever (approximately 1% per annum). In both studies, the protective efficacy of the Vi capsular polysaccharide was about 70%. About 75% of subjects in these areas responded with a four-fold or greater rise of serum Vi capsular polysaccharide antibodies. In contrast, the Vi capsular polysaccharide elicited a four-fold or greater rise in 95–100% of young adults in France and the United States.

The present invention provides method to synthesize Vi capsular polysaccharide-protein conjugates in order to enhance antibody response and to confer T-dependent properties to the Vi capsular polysaccharide. According to the present invention, a heterobifunctional crosslinking reagent, such as N-succinimidyl 3-(2-pyridyldithio) propionate (SPDP), is used to bind thiol derivatives of the Vi capsular polysaccharide to proteins. This synthesis was reproducible, provided high yields of Vi-protein conjugates, and was applicable to several medically relevant proteins, such as diphtheria and tetanus toxoids. The resultant conjugates were more immunogenic in mice and juvenile Rhesus monkeys than the Vi alone. The process of the present invention can also be used to synthesize protein conjugates with other polysaccharides that have carboxyl functions.

Vaccines can be produced from the protein conjugates of the present invention by adding the protein conjugate to a pharmaceutically acceptable carrier, such as saline or the like. The immunization may be effected by injecting the host one, two, or three times at two week intervals. A sufficient dose of the protein conjugates may range from about 1 microgram per kg of body weight to about 1000 micrograms per kg of body weight.

While the invention is described above in relation to certain specific embodiments, it will be, understood that many variations are possible, and that alternative materials and reagents can be used without departing from the invention. In some cases such variations and substitutions may require some experimentation, but some will only involve routine testing.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology employed herein is for the purpose of description and not of limitation.

What is claimed is:

1. A method for conjugating capsular polysaccharide having carboxyl groups to a protein comprising:
   (a) forming a thiol derivative of the carboxyl groups of the polysaccharide; and
   (b) binding said thiol derivative to a protein using a heterobifunctional crosslinking agent.

2. The method of claim 1 wherein the crosslinking agent is N-succinimidyl 3-(-2-pyridyldithio)propionate.

3. The method of claim 1 wherein the capsular polysaccharide is Vi capsular polysaccharide.

4. The method of claim 3 wherein the protein is tetanus toxoid.

5. The method of claim 3 wherein the protein is diphtheria toxoid.

6. The method of claim 3 wherein the protein is selected from the group consisting of cholera toxin and β-subunit of cholera toxin.

7. The method of claim 3 wherein the protein is *Haemophilus influenzae* type b protein.

8. The method of claim 3 wherein the protein is IgG.

9. A composition for enhancing the antibody response of a host comprising a capsular polysaccharide having carboxyl groups conjugated through a thio derivative of said carboxyl groups to a protein in a physiologically acceptable carrier.

10. A method of enhancing the antibody response of a host comprising injecting said host with a composition according to claim 9.

11. The method of claim 10 wherein the host is injected at least two times at two week intervals.

12. The composition of claim 9 wherein the capsular polysaccharide is Vi capsular polysaccharide.

13. The composition of claim 12 wherein the protein is tetanus toxoid.

14. The composition of claim 12 wherein the protein is diphtheria toxoid.

15. The composition of claim 12 wherein the protein is selected from the group consisting of toxin and β-subunit of cholera toxin.

16. The composition of claim 12 wherein the protein is *Haemophilus influenzae* type b protein.

17. The composition of claim 12 wherein the protein is IgG.

18. The composition of claim 1 wherein the thiol derivative is formed by reducing a cystamine amide of the carboxyl groups.

* * * * *

UNITED STATES PATENT AND TRADEMARK OFFICE
CERTIFICATE OF CORRECTION

PATENT NO. : 5,204,098
DATED : APRIL 20, 1993
INVENTOR(S) : SHOUSUN C. SZU, RACHEL SCHNEERSON and JOHN B. ROBBINS It is certified that error appears in the above-identified patent and that said Letters Patent is hereby corrected as shown below:

Claim 9, Column 14, line 9, "thio" should read --thiol--.

Claim 15, Column 14, line 24, "toxin" should read --cholera toxin--.

Signed and Sealed this

Twelfth Day of April, 1994

Attest:

BRUCE LEHMAN

Attesting Officer

Commissioner of Patents and Trademarks